United States Patent
Spreeuwers et al.

(10) Patent No.: US 7,376,253 B2
(45) Date of Patent: May 20, 2008

(54) ANALYSIS OF SUCCESSIVE DATA SETS

(75) Inventors: Lieuwe Jan Spreeuwers, Amersfoort (NL); Marcel Breeuwer, Eindhoven (NL); Eltjo Hans Haselhoff, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 682 days.

(21) Appl. No.: 10/071,424

(22) Filed: Feb. 8, 2002

(65) Prior Publication Data
US 2002/0168095 A1 Nov. 14, 2002

(30) Foreign Application Priority Data
Feb. 13, 2001 (EP) .................................. 01200517

(51) Int. Cl.
*G06K 9/00* (2006.01)
(52) U.S. Cl. ....................... 382/131; 382/100; 382/128
(58) Field of Classification Search ........ 382/128–134, 382/107, 282, 195
See application file for complete search history.

(56) References Cited

U.S. PATENT DOCUMENTS

| | | | | |
|---|---|---|---|---|
| 5,273,040 A | * | 12/1993 | Apicella et al. ............ | 600/410 |
| 5,343,390 A | * | 8/1994 | Doi et al. .................... | 382/132 |
| 5,360,006 A | * | 11/1994 | Geiser et al. ............... | 600/425 |
| 5,431,161 A | | 7/1995 | Ryals | |
| 5,509,084 A | | 4/1996 | Tanaka | |
| 5,570,430 A | * | 10/1996 | Sheehan et al. ............ | 382/128 |
| 5,669,382 A | | 9/1997 | Curwen | |
| 5,734,739 A | * | 3/1998 | Sheehan et al. ............ | 382/128 |
| 5,797,396 A | * | 8/1998 | Geiser et al. ............... | 600/407 |
| 5,818,896 A | | 10/1998 | Hsieh | |
| 6,065,475 A | | 5/2000 | Qian | |
| 6,278,767 B1 | * | 8/2001 | Hsieh ......................... | 378/163 |
| 6,292,683 B1 | * | 9/2001 | Gupta et al. ................ | 600/410 |
| 6,718,055 B1 | * | 4/2004 | Suri ............................ | 382/128 |

FOREIGN PATENT DOCUMENTS

WO 1996038815 A1 12/1996

OTHER PUBLICATIONS

"Image Sequence Segmentation Based on 2D Temporal Entropic Thresholding", Jianping Fan et al, Pattern Recognition Letters, vol. 17, No. 10, Sep. 2, 1996, pp. 1101-1107.
"Spatio-Temporal Image Segmentation Using Optical Flow and Clustering Algorithm", Galic et al, Proceedings of the First International Workshop on Image and Signal Processing and Analysis, Jun. 14-15, 2000, pp. 63-68.

(Continued)

*Primary Examiner*—Matthew C. Bella
*Assistant Examiner*—Shefali Patel

(57) ABSTRACT

The invention relates to the analysis of successive data sets. A local intensity variation is formed from such successive data sets, that is, from data values in successive data sets at corresponding positions in each of the data sets. A region of interest is localized in the individual data sets on the basis of the local intensity variation. In particular the time derivative of the local intensity variation is used to localize the region of interest. The invention can be used notably for cardiological applications so as to separate the image of the myocardium from a sequence of 3D magnetic resonance reconstruction images.

17 Claims, 2 Drawing Sheets

OTHER PUBLICATIONS

Figure 1:
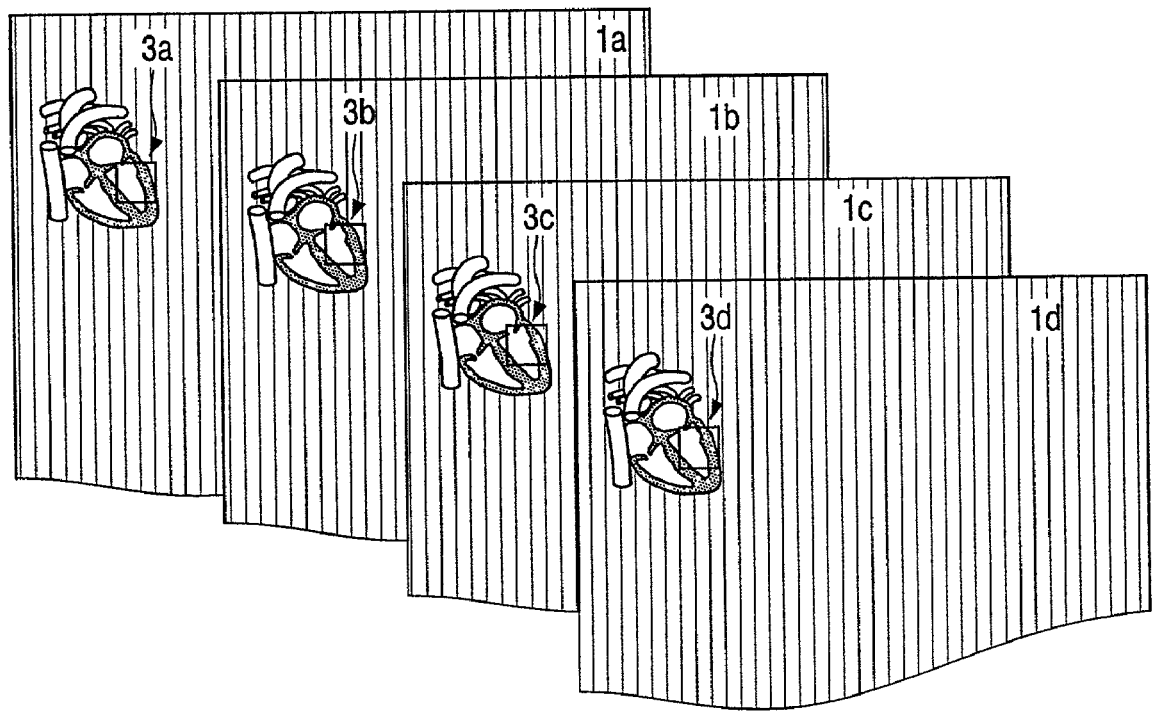

Cootes et al. "Active Shape Models - Their Training and Application", Computer Vision and Image Understanding vol. 61, No. 1, Jan. 1995, pp. 38-59.

Boyle et al. "Automated Analysis of Contrast Echocardiographic Time-Intensity Curves to Predict Myocardial Perfusion" Depart. of Medicine, Cardiology Section, pp. 203-206.

Sorgel, W. "Automatic Heart Localization from a 4D MR Dataset", SPIE vol. 3034, pp. 333-344.

Weng, John et al "Learning-Based Ventricle Detection from Cardiac MR and CT Images", IEEE Trans. on Medical Imaging, vol. 16, No. 4, Aug. 1997, pp. 378-391.

Suri, Jasjit S. et al, "Recent-Advances towards a Model-Based Pattern-Recognition Approach for the Left Ventricle Boundary Estimation", Intl Conf. on Advances in Pattern recognition, 1998, pp. 135-144.

IP, Horace H.S. et al "Segmentation of the Aorta Using a Temporal Active Contour Model with Regularisation Scheduling", SPIE vol. 3034, pp. 323-332.

Malassiotis S. et al "Tracking the left Ventricle in Echocardiographic Images by Learning Heart Dynamics", IEEE Trans. on Medical Imaging, vol. 18, No. 3, Mar. 1999, pp. 282-290.

* cited by examiner

ANALYSIS OF SUCCESSIVE DATA SETS

The invention relates to a method of analyzing successive data sets, in which the individual data sets comprise data elements which assign data values to spatial positions.

A method of this kind is known from U.S. Pat. No. 5,431,161.

The known method utilizes data sets acquired by means of a Single Photon Emission Computed Tomography (SPECT) imaging method. The known method is intended notably for the diagnosis of cardiac diseases, notably diseases of the coronary arteries. The SPECT imaging method is used to form SPECT images of cross-sections of the heart of a patient to be examined. Subsequently, the user of the known method has to select regions of interest from the SPECT images by hand. The regions of interest are notably the parts of the SPECT images which relate to the myocardium (the heart muscle). The known method subsequently determines the perfusion of the myocardium so as to obtain an idea of the degree of perfusion of the cardiac muscle. To this end, the ratio of the mean brightnesses of the brightest part of the SPECT images is determined in the end systolic phase and the end diastolic phase of the heart to be examined.

It is an object of the invention to provide a method which enables more accurate analysis of the data sets. It is notably an object of the invention to provide a method which enables more exact localization of the region of interest in the successive data sets.

This object is achieved by means of a method of analyzing successive data sets, in which a local intensity variation $[I(x,t)]$ is established from data values in successive data sets in corresponding spatial positions, and on the basis of the local intensity variation a region of interest is localized from one or more of the successive data sets, the local intensity variation in the region of interest is in conformity with a predetermined property.

In accordance with the invention the region of interest is localized in the successive data sets on the basis of the local intensity variation of the data values in the data sets. The invention can be advantageously used in particular when each of the data sets represents an image of an object to be examined. In that case the data values are brightness values or grey values of the pixels of the image. The invention, however, can also be used when the data values represent the local value of a physical quantity; such a quantity may be, for example, the temperature, pressure, concentrations of given substances and so on. The intensity variation represents the variations of data values in successive data sets in corresponding positions. For example, when the data sets succeed one another in time, the intensity variation represents the variation in time of the data values in corresponding positions. The invention can be advantageously used, for example, for magnetic resonance perfusion imaging methods; the successive data sets then relate to successive phases of a perfusion process. The data sets are then acquired by reconstruction from magnetic resonance signals acquired during the successive phases of the perfusion process while utilizing a perfusion-sensitive magnetic resonance imaging method. The approach in accordance with the invention is based on the recognition of the fact that a difference exists between the variation in time of the data values in the region of interest and that of the data values outside the region of interest. It even often happens that a given characteristic intensity variation occurs in the region of interest. It has been found that such a characteristic intensity variation can be readily localized, that is, in particular by comparing the instantaneous intensity variation with a predetermined intensity variation. It usually suffices to limit this comparison to one or a few characteristic properties of the intensity variation.

These and other aspects of the invention will be described in detail hereinafter on the basis of the following embodiments which are defined in the dependent claims.

The local intensity variation is preferably established for different blocks which relate to large or small spatial regions, but preferably comprise a plurality of data values of the individual data sets. This step is preferably taken in situations in which the local intensity variation changes significantly across significant spatial distances but only slightly across shorter distances. Consequently, it is not necessary to determine the local intensity variation for each of the individual spatial positions, so that the number of calculations required so as to obtain the local intensity variation is limited. The size of the blocks preferably amounts to approximately the distance over which significant differences occur in the local intensity variation. Suitable results are obtained by means of non-overlapping blocks of approximately 32×32 image elements (pixels). The locally averaged local intensity variation in these individual blocks is calculated. To this end, respective local mean values of the data values are calculated in the individual data sets in the individual blocks. The local mean intensity variation is derived from said local mean data values. The local mean data values are obtained for each block in the individual data sets by filtering while using, for example, a Gaussian profile. Incidental fluctuations, such as caused by noise, are thus prevented from affecting the localization of the region of interest.

The time derivative of the local intensity variation constitutes a suitable characteristic property of the local intensity variation. In many situations the time derivative of the local intensity variation in the region of interest is clearly distinct from the time derivative of the local intensity variation outside the region of interest. The time derivative of the local intensity variation is notably very suitable for use in cardiology. A variety of radiological techniques, such as magnetic resonance angiography, X-ray angiography or computed tomography angiography, enable the acquisition of successive data sets in which the heart of a patient to be examined is imaged. The data values in the data set then represent local intensity values in the angiographic image. Such an image concerns, for example, a cross-section of the heart of the patient to be examined, but it is also possible to form a spatial (three-dimensional) image of the heart of the patient to be examined. In these applications regions of interest are, for example, the parts in the data sets which relate to the left ventricle and to the right ventricle and to the myocardium of the heart of the patient to be examined. Furthermore, a contrast medium is administered to the patient for the acquisition of the data sets. The local intensity variation then represents the passage of blood with the contrast medium through the individual anatomical parts of the heart of the patient to be examined. Furthermore, considerable differences exist between the local intensity variations in the individual anatomical parts of the heart. For example, first a significant fast increase of the intensity occurs, succeeded by a somewhat slower decrease of the intensity in the left ventricle. Such an intensity profile also occurs in the right ventricle, be it with a given time delay, and this intensity profile occurs even later in the myocardium, be it with less strong variations in time of the intensity. In accordance with the invention the left and right ventricles and the myocardium can thus be localized accurately and automatically on the basis of an angiographic (cardio) data set.

Considerable differences occur notably between the time derivatives of the local intensity profile in the left ventricle and in the right ventricle, respectively, the myocardium and the region outside the heart of the patient to be examined. Consequently, the time derivative of the local intensity variation is very suitable for accurately and automatically localizing the left and right ventricles and the myocardium from an angiographic (cardio) data set.

It is notably possible to localize the region of interest on the basis of blocks of data elements in which the variations of the local intensity variation, for example, the time derivative of the local intensity variation, exceed a predetermined ceiling value and/or are smaller than a predetermined bottom value. In the cardiological application of angiography in particular, for example, the left ventricle and the right ventricle can be localized in this manner. In the left ventricle and the right ventricle a fast, significant increase takes place, followed by a significant decrease of the local intensity; this means that the ceiling value is exceeded by the time derivative of the local intensity variation, followed by a value of the time derivative which is lower than the bottom value. This bottom value is preferably negative. Parts in the data sets in which a decreasing intensity variation occurs can thus be localized. Such a decreasing intensity variation occurs, for example, because the concentration of contrast medium in the blood in the heart of the patient to be examined decreases after the passage of a contrast bolus. In practice it often suffices to localize only the left and the right ventricle from the successive data sets on the basis of the time derivative of the local intensity variation. The myocardium can subsequently be localized on the basis of the position of the left ventricle and that of the right ventricle which have meanwhile been determined.

In accordance with the invention the local intensity variation can be used to classify the data elements as belonging to the region of interest or not. For example, because values of the time derivative occur which exceed the ceiling values and also negative values of the time derivative which are below the bottom value, data elements can be readily classified as belonging to the left ventricle or to the right ventricle.

In a further advantageous implementation of the method in accordance with the invention the local intensity variation is compared with a reference intensity variation for the region of interest. Such a mean intensity variation is determined in advance, for example, empirically. For example, the intensity variations in the left and right ventricles and the myocardium are empirically determined for a large number of patients. For the individual parts of the heart individual mean intensity variations are formed from such empirically determined intensity variations. Such mean intensity variations can be suitably used as a reference.

It has been found that the comparison of the local intensity variation and the reference intensity variation can be accurately performed by comparing the time derivative of the local intensity variation with the time derivative of the reference intensity variation.

The data elements can be accurately classified without requiring much calculation work by comparing the local intensity variation for the relevant data element with the reference intensity variation. For example, the comparison is performed by calculating the correlation between the local intensity variation and the reference intensity variation. This comparison can be performed accurately and quantitatively in particular by means of a similarity measure. Such a similarity measure indicates the degree of correspondence between the local intensity variation and the reference intensity variation.

In an advantageous implementation of the method in accordance with the invention strong spatial gradients of data values are masked in parts of the data sets. In this context the term "mask" is to be understood to mean that such strong spatial gradients are omitted or ignored for the further operations. Such strong spatial gradients, in conjunction with the consequences of motion, for example, during the acquisition of the data values, may give rise to significant artificial temporal gradients. When parts in the individual data sets with strong spatial gradients of the data values are masked, the adverse effects of such artificial temporal gradients on the localization of the region of interest are avoided. Masking is performed, for example, by calculating local mean gradients in the data set and subtracting the local mean gradients from the data values in the data sets. In circumstances where it is known in advance that the region of interest itself is (also) characterized by strong spatial gradients, this aspect can be taken into account. For example, in the case of MR angiography with perfusion, masking is limited to the data sets prior to the occurrence of perfusion and/or after termination of the perfusion.

Preferably, the data sets are mutually corrected for phenomena which are due to motion, for example, during the acquisition of the data set. Such a correction is also referred to as "mutual registration". Shifts in time are performed in successive data sets, that is, the spatial positions whereto the data values are assigned are adapted in such a manner that corresponding parts in successive data sets are situated each time in the same spatial positions. Such corresponding parts relate, for example, each time to one and the same (part of an) object reproduced by the data set at successive moments in time.

The method in accordance with the invention is also suitable for localizing a plurality of different regions of interest from the successive data sets. It is notably possible to localize different regions of interest where differences exist between the local intensity variations in such different regions. This occurs notably in cardiological angiography in which the successive data sets relate to the passage of blood with contrast medium through the left ventricle and the right ventricle and the myocardium of the heart of the patient to be examined. Such individual regions of interest are accurately localized by means of the method in accordance with the invention. The corresponding regions of interest in the individual data sets are preferably mutually registered so as to correct for artificial phenomena that are caused by motions, such as the beating of the heart and respiration of the patient to be examined. In conformity with an advantageous implementation of the method in accordance with the invention maximum intensity projections are formed in a direction of succession through the successive data sets of the individual spatial regions of interest that have already been localized. Differences between such individual maximum intensity projections constitute feature images in which each time one of the regions of interest is reproduced in an intensified manner. It is notably possible to reproduce individual regions of interest in an intensified manner relative to other localized regions of interest in situations in which the individual regions of interest exhibit each time a similar intensity variation, be it with a delay in time. Such a situation occurs notably in cardiological angiography where perfusion of blood with contrast medium first takes place through the right ventricle, and subsequently through the left ventricle and ultimately through the myocardium. When a maximum intensity projection through the successive data sets of the left ventricle and the right ventricle is formed in the period of time between the passage through the left ventricle and the right ventricle, that is, of the regions relating to the left ventricle and the right ventricle, and when this projection is subtracted from another maximum intensity projection, at an instant after the passage through the left ventricle, through the successive data sets of the regions of interest that relate to the left ventricle, a feature image is formed in which the left ventricle and the myocardium are reproduced in an intensified fashion. It has been found that the general shape of the region of interest is often known in advance, notably in the case of cardiological applications; for example, the region of interest has a more or less round shape. The boundary can be easily derived from the feature image while utilizing the general shape that is known in advance. Notably interpolation with a restriction to the known shape is suitable for this purpose. Interpolation on the basis of a so-called statistical shape model is also suitable to determine the boundary. Such a statistical shape model is known per se from T. F. Cooten et al. "*Active shape models—their training and application*", Comp. Vis. Image Underst. 61(1):38:59, 1995. and also from A. D. Brett and C. J. Taylor, "*Automated construction of 3D shape models using harmonic maps*", in Medical Image Understanding and Analysis, London, July 2000, pp. 175 to 178.

The edge of the region of interest can be readily localized by transforming the feature image, in which the round region of interest is reproduced in intensified form, to pole co-ordinates. Preferably, the origin of the pole co-ordinate system is chosen to be situated at the center of the round region in the feature image. The edge of the region of interest appears as a distinct transition in the data values in the feature image that has been transformed to pole co-ordinates; this transition appears as a straight edge in a rendition. Such a straight edge can be readily localized. Thus, in particular it is easy to localize the region of the myocardium exactly in the feature image. Subsequently, the local perfusion of the myocardium can be studied.

In an advantageous implementation of the invention a mask is derived for one or more of the individual data sets, that is, on the basis of the time derivative of the local intensity variation. Values for the mask are determined for individual spatial positions and from the value of the time derivative of the local intensity variation at the area of the relevant spatial position in the individual data set. Such a mask is used to segment the region of interest from the relevant data set. For example, the mask is formed as a binary data set. The segmentation is then performed by retaining in the relevant data set the data values for spatial positions for which the mask has the same value, for example the value 1. The mask can be obtained simply by applying a threshold filter to the time derivative of the local intensity variation, so that only the values of the time derivative of the local intensity variation which are larger or smaller than a predetermined limit value are retained for the relevant data set.

In a further advantageous implementation of the invention the spatial distribution of the time derivative of the local intensity variation is reproduced as an image for one or more of the data sets. Notably the value of the maximum of the time derivative of the local intensity variation is shown at the relevant spatial position or for the relevant block. Such an image is also referred to as an "upslope map". The foregoing can be carried out very well by utilizing so-called false colors; in that case the color values represent the local value of the time derivative of the local intensity variation. In cardiological applications such an upslope map is preferably formed for the region of interest relating to the myocardium. This upslope map is a suitable rendition of the perfusion of the myocardium and hence constitutes a suitable technical aid for the cardiologist for localizing infarcted regions and the extent of the infarction.

The invention also relates to an analysis system for carrying out the method in accordance with the invention. Such an analysis system in accordance with the invention is defined in claim 16. An analysis system of this kind is preferably configured as a medical diagnostic workstation. The invention also relates to a computer program for analyzing successive data sets. Such a computer program in accordance with the invention is defined in claim 17. For example, a computer program in accordance with the invention can be loaded into the memory of an analysis system, for example, a medical diagnostic workstation. The computer program in accordance with the invention can be stored on a data carrier, for example, a CD-ROM disc, and be downloaded into the memory of the analysis system from the data carrier. It is also possible to download the computer program from a network such as the "world-wide web".

Figure 4:
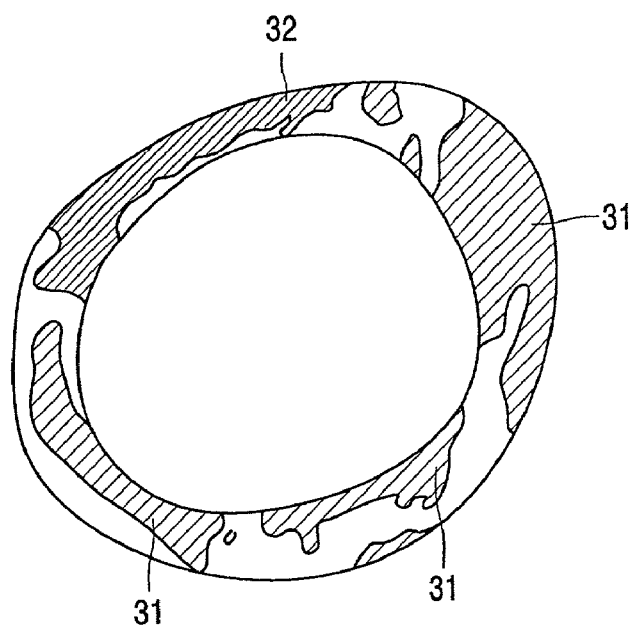
Figure 2:
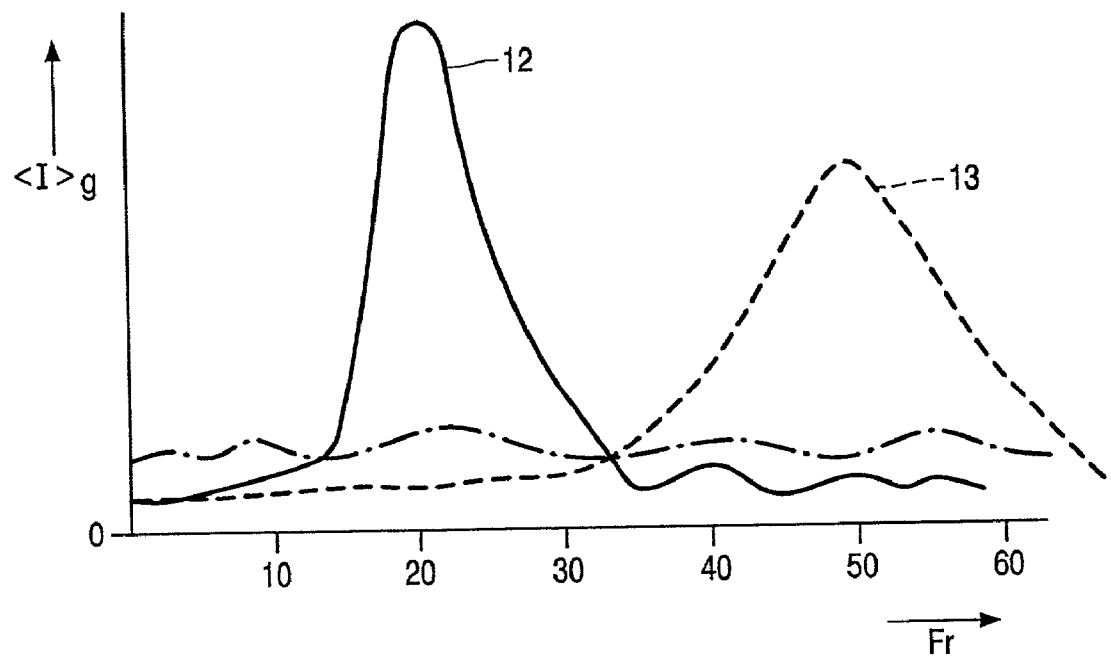
Figure 3:
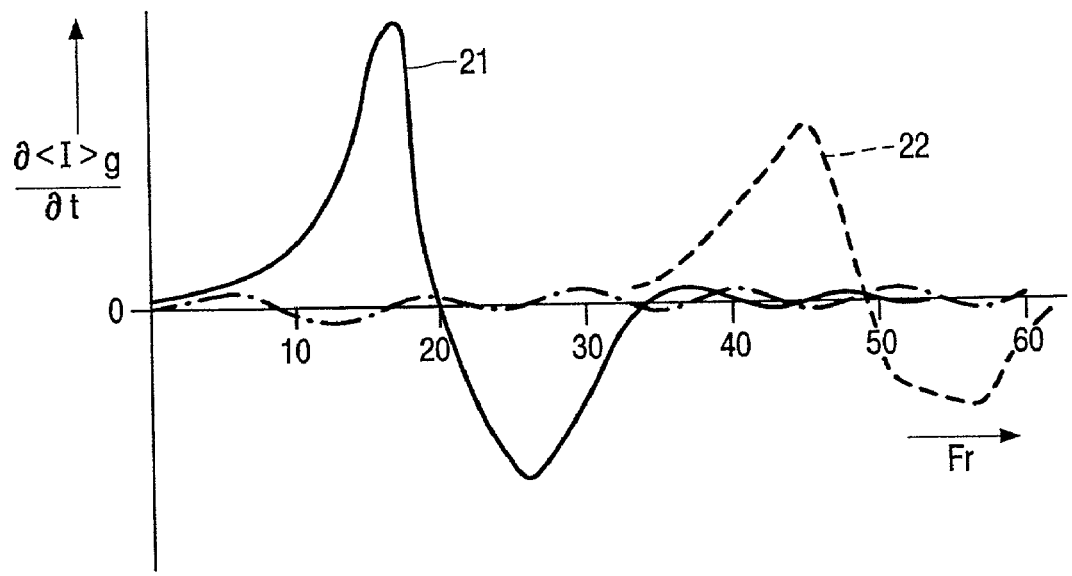

These and other aspects of the invention will be described in detail hereinafter, by way of example, on the basis of the following embodiments and with reference to the accompanying drawing; therein FIG. 1 shows an example of successive data sets whereto the invention is applied, FIG. 2 shows examples of the local intensity variation, FIG. 3 shows examples of the time derivative of the local intensity variation, and FIG. 4 shows an example of an upslope map.

FIG. 1 shows an example of successive data sets whereto the invention is applied. Each of the data sets 1a, 1b, 1c and 1d in FIG. 1 represents an image of a cross-section of the heart 10 of the patient to be examined. These images are notably magnetic resonance images or CT images. The data sets, or images, in the example of FIG. 1 are successive in time, that is, the image 1b succeeds the image 1a while the image 1c succeeds the image 1b and the image Id succeeds the image 1c. Only four data sets are shown for simplicity of the Figure, but many tens or hundreds of successive data sets may be used in practice.

Each time blocks 3a, 3b, 3c, 3d of data values are taken in the data sets. In FIG. 1 each time one of the blocks is shown in each of the data sets; in particular, the block 3a, 3b, 3c, 3d shown is situated at the area of the left ventricle 11 of the heart 10. The weighted mean data value is calculated for each of the blocks 3a, 3b, 3c, 3d by Gaussian filtering. The local intensity variation is obtained for the blocks 3a, 3b, 3c, 3d by plotting said weighted mean values as a function of time; this is represented by the solid curve 12 in FIG. 2. Therein, the sequence number of the successive data sets, or images (also referred to as frames), is plotted along the time axis. As appears from FIG. 2, and also from FIG. 3, successive data sets with more than 60 individual data sets or images are used for the present example. The local intensity variation 12 as shown in FIG. 2 exhibits a strong maximum which corresponds to the bolus passage through the left ventricle. The dashed curve 13 in FIG. 2 represents the local intensity variation at the area of the right ventricle. The maximum of the local mean data values now occurs only at approximately the $50^{th}$ frame, because the contrast bolus traverses the right ventricle later than the left ventricle.

FIG. 3 shows the time derivatives 21, 22 of the local intensity variation. Each of the time derivatives 21, 22 has the property that a high positive maximum is succeeded by a strong negative minimum. The local intensity variations at the area of the left ventricle and the right ventricle can be readily localized on the basis of this property. For the purpose of comparison a dash-dot line is plotted so as to represent the local intensity variation outside the heart, in this case being the brightness value, that is, the data value which is approximately constant in the map.

In accordance with the invention the local intensity variation is determined for many blocks in each of the data sets, that is, by comparison with a reference. This comparison is carried out, for example, while utilizing the similarity measure. To this end, an overlap of the time derivative of the relevant local intensity variation p and the time derivatives of the reference intensity variation q is determined:

$$O = \frac{\min(p_{end}, q_{end}) - \max(p_{start}, q_{start})}{\max(p_{end} - p_{start}, q_{end} - q_{start})}$$
$$0 \ (p_{end} \le q_{start}, q_{end} \le p_{start})$$

Therein, the subscripts "end" and "start" indicate the selected end instant and start instant of the local intensity variation and the reference intensity variation. The overlap O is zero when the local intensity variation commences before or terminates after the reference intensity variation. The overlap indicates to what extent the support of the local intensity variation in the successive data sets, for example, in time, coincides with the support of the reference intensity variation. A suitable similarity measure is:

$$S = H(O - O_{min}) H(t_{max} - t_{min})(p_{max} - p_{min})$$

Therein, H is the heavy side step function $$H(x) = \begin{cases} 0 & x \le 0 \\ 1 & x \ge 0 \end{cases},$$

and $p_{max}$ and $p_{min}$ are the values of the local maximum and the local minimum in the time derivative of the local intensity variation. In the case of the application for cardiology, this maximum and minimum relate to the arrival of the contrast bolus and the departure of the contrast bolus, respectively. The parameter $O_{min}$ is a minimum overlap with the time derivative of the reference intensity variation. The similarity measure S takes into account the fact that the minimum succeeds the maximum in the time derivative of the local intensity variation. Using the similarity measure, data values in the data sets or pixels in the successive images are classified as belonging to the region of interest, for example, the image of the left ventricle.

FIG. 4 shows an example of an upslope map. This upslope map concerns the myocardium. Therein, the part of the myocardium which is reproduced in the images is localized in advance as the region of interest. Subsequently, the value of the maximum of the time derivative of the local intensity variation is locally reproduced as a "false" color or grey value in the image of the myocardium. It is clearly shown that there are parts 31 with a suitable perfusion; in these parts rather high maximum values of the time derivative of the local intensity variation occur. In other regions 32 the perfusion obviously is less good, because in these regions the maximum values reached for the time derivative are not as high by far.

The invention claimed is:

1. A method of analyzing successive data sets, where each of the individual data sets comprise data elements which assign data values to spatial positions, the method comprising the steps of:
   calculating weighted mean data value for each of a plurality of establishing a local intensity variation [l(x, t)] from data values in successive data sets in corresponding spatial positions, and
   localizing a region of interest on the basis of a time derivative of the local intensity variation from one or more of the successive data sets, wherein the local intensity variation in the region of interest is in conformity with a predetermined property.

2. A method of analyzing successive data sets as claimed in claim 1, wherein the step of establishing the local intensity variation is carried out for respective blocks of several data elements.

3. A method of analyzing successive data sets as claimed in claim 1, wherein the step of localizing includes localizing the region of interest on the basis of variations in the local intensity variation, notably on the basis of a time derivative $$\frac{\partial I(x,t)}{\partial t}$$

of the local intensity variation.

4. A method of analyzing successive data sets as claimed in claim 3, wherein the step of localizing the region of interest includes localizing blocks of data elements in which the variations in the local intensity variation are larger than a predetermined ceiling value and/or by localizing blocks of data elements in which the variations in the local intensity variation are smaller than a predetermined bottom value.

5. A method as claimed in claim 3, wherein a mask is derived from the time derivative of the local intensity variation for an individual data set, and
   the region of interest is segmented from the relevant data set by means of the mask.

6. A method as claimed in claim 5, wherein the mask is derived by applying a threshold filter to the time derivative of the local intensity variation for the relevant data set.

7. A method as claimed in claim 3, wherein a spatial distribution of the time derivative of the local intensity variation is reproduced for an individual data set.

8. A method of analyzing successive data sets as claimed in claim 1, further including a step of classifying data elements in one or more individual data sets, the classification of the data elements in the relevant data set (sets) indicating whether the relevant data element belongs to the region of interest or not.

9. A method of analyzing successive data sets as claimed in claim 8, wherein the step of classifying includes performing the classification is on the basis of a measure of similarity of the local intensity variation and a reference intensity variation in the region of interest.

10. A method of analyzing successive data sets as claimed in claim 8, wherein the step of classifying includes performing the classification is on the basis of a correlation of the local intensity variation with a mean intensity variation in the region of interest.

11. A method of analyzing successive data sets as claimed in claim 1, further including a step of masking parts with spatial gradients of data values in individual data sets in as far as the modulus of the spatial gradients in the relevant parts exceeds a predetermined acceptable gradient modulus.

12. A method of analyzing successive data sets as claimed in claim 1, wherein said successive data sets are made to correspond to one another.

13. A method of analyzing successive data sets, comprising the steps of:
   localizing a plurality of regions of interest on the basis of a time derivative of local intensity variation, wherein the local intensity variation in said regions of interest being in conformity with a predetermined property,
   determining maximum intensity projections (MIPs) for the respective regions of interest, and
   forming a feature image from differences between said maximum intensity projections.

14. A method of analyzing successive data sets as claimed in claim 13, wherein a center of the region of interest is determined in the feature image.

15. A method of analyzing Successive data sets as claimed in claim 14, wherein the feature image is transformed to pole co-ordinates with said center as the origin, and
   a boundary of the region of interest is localized in said transformed feature image.

16. An analysis system for analyzing successive data sets, wherein individual data sets comprise data elements which assign data values to spatial positions, comprising:
   means to establish a local intensity variation $[l(x,t))]$ from data values in successive data sets in corresponding spatial positions, and
   means for localizing, a region of interest from one or more of the successive data sets on the basis of a time derivative of the local intensity variation, wherein the local intensity variation in the region of interest is in conformity with a predetermined property.

17. A computer-readable medium for storing a set of computer instructions, which instructions are capable of implementing a method of analyzing successive data sets, including individual data sets with data elements that assign data values to spatial positions, comprising:
   establishing a local intensity variation $[l(x,t)]$ from data values in successive data sets in corresponding spatial positions, and
   localizing, on the basis of a time derivative of the local intensity variation, a region of interest from one or more of the successive data sets, wherein the local intensity variation in the region of interest being in conformity with a predetermined property.

* * * * *